(12) United States Patent
Peterson

(10) Patent No.: US 6,402,676 B2
(45) Date of Patent: Jun. 11, 2002

(54) TIP CONFIGURATION FOR RADIATION SOURCE WIRES

(75) Inventor: Eric D. Peterson, Fremont, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 09/233,827

(22) Filed: Jan. 20, 1999

(51) Int. Cl.$^7$ ................................................ A61N 5/00
(52) U.S. Cl. ......................................................... 600/3
(58) Field of Search ................................ 600/1–3, 4–8

(56) References Cited

U.S. PATENT DOCUMENTS

| | | | |
|---|---|---|---|
| 5,114,423 A | * | 5/1992 | Kasprzyk et al. ............. 606/27 |
| 5,158,548 A | | 10/1992 | Lau et al. |
| 5,199,939 A | | 4/1993 | Dake et al. |
| 5,344,426 A | | 9/1994 | Lau et al. |
| 5,354,257 A | | 10/1994 | Roubin et al. |
| 5,360,401 A | | 11/1994 | Turnland |
| 5,411,466 A | | 5/1995 | Hess |
| 5,421,955 A | | 6/1995 | Lau et al. |
| 5,484,384 A | | 1/1996 | Fearnot |
| 5,498,227 A | * | 3/1996 | Mawad ........................... 600/3 |
| 5,514,154 A | | 5/1996 | Lau et al. |
| 5,688,220 A | * | 11/1997 | Verin et al. ..................... 600/1 |
| 5,910,101 A | * | 6/1999 | Andrews et al. ............... 600/3 |
| 6,024,690 A | | 2/2000 | Lee et al. |
| 6,048,299 A | | 4/2000 | Hoffman |

* cited by examiner

Primary Examiner—Max Hindenburg
(74) Attorney, Agent, or Firm—Blakely, Sokoloff, Taylor & Zafman LLP

(57) ABSTRACT

The invention is directed to a radiation source for delivery of a radiation treatment to a body lumen. The radioactive tip of the source wire is detachable from the main portion of the core wire to allow the radioactive source in the tip to be sterilized and re-sterilized independently of the core wire. The detachable radioactive tip also includes a flexible portion for improved tracking through a lumen of a catheter.

24 Claims, 2 Drawing Sheets

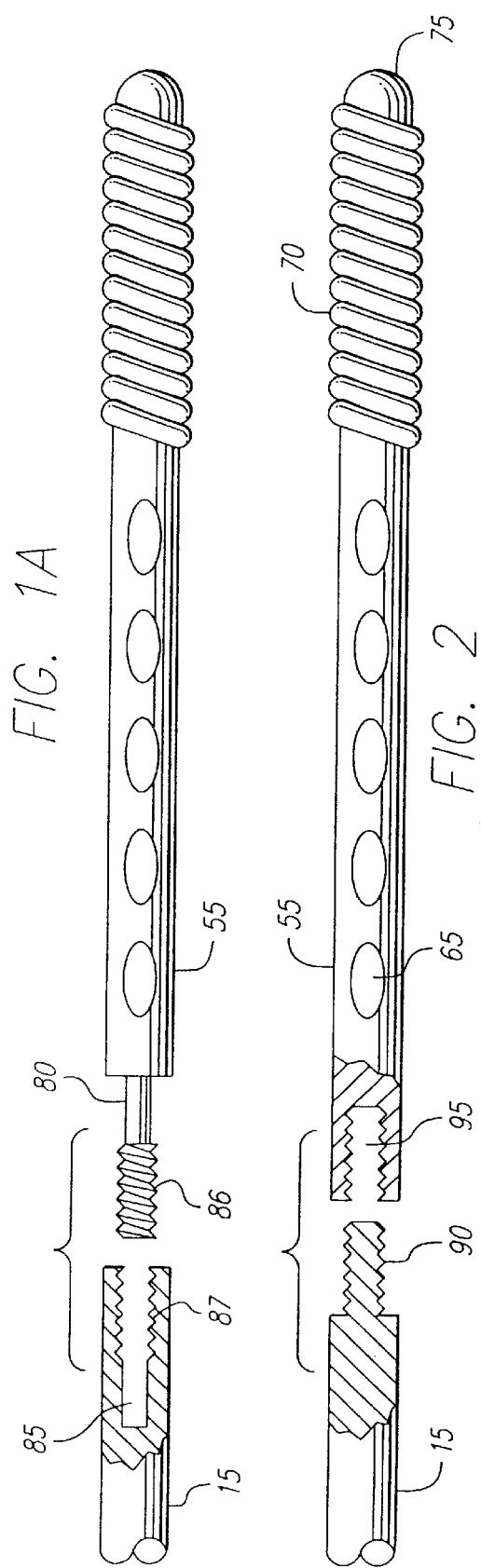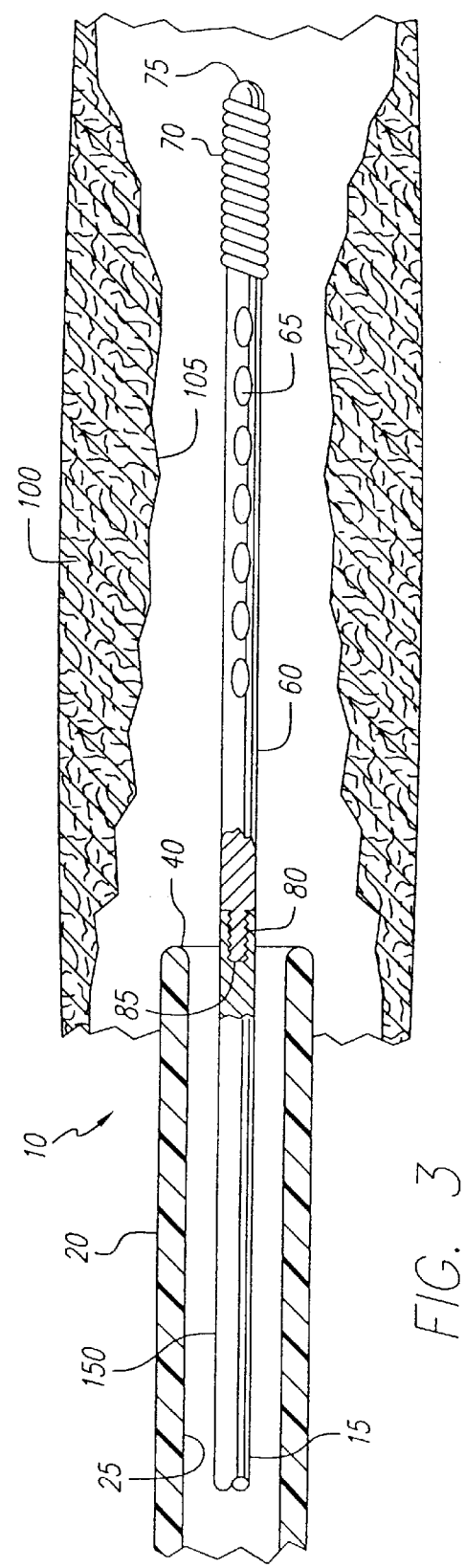

TIP CONFIGURATION FOR RADIATION SOURCE WIRES

BACKGROUND OF THE INVENTION

This invention generally relates to intravascular catheters for treating a portion of a body lumen with radiation and particularly to an intravascular catheter and guide wire suitable for delivering a radiation source to the body lumen which utilizes a detachable tip to facilitate re-sterilization of the radiation tip to allow for re-use of the radiation source.

In percutaneous transluminal coronary angioplasty (PCTA) procedures, a guiding catheter having a preshaped distal tip is percutaneously introduced into the cardiovascular system of a patient through the brachial or femoral artery and is advanced therein until the preshaped distal tip is disposed within the aorta adjacent to the ostium of the desired coronary artery. The guiding catheter is then twisted and torqued from its proximal end to turn its distal tip so that it can be guided into the coronary ostium. In an over-the-wire dilatation catheter system, a guide wire and a dilatation catheter having an inflatable balloon on the distal end thereof are introduced into, and advanced through, the proximal end of the guiding catheter to the distal tip of the guiding catheter seated within the coronary ostium. The distal tip of the guide wire is usually manually shaped (i.e., curved) by the physician or one of the attendants before it and the dilatation catheter are introduced into the guiding catheter. The guide wire is usually first advanced out of the distal end of the guiding catheter and is maneuvered into the patient's coronary vasculature containing the stenosis to be dilated, and is then advanced beyond the stenosis. Thereafter, the dilatation catheter is advanced over the guide wire until the dilatation balloon is positioned across the stenosis. Once the dilatation catheter is in position, the balloon of the catheter is filled with inflation fluid at relatively high pressures (e.g., generally about 4–10 atmospheres) to inflate it to a predetermined size (preferably the same as the normal inner diameter of the artery at that particular location) in order to radially expand the lumen at the stenosis, thereby increasing the effective diameter of the occluded artery. The balloon can then be deflated so that the catheter can be removed and blood flow resumed through the dilated artery.

One common problem that sometimes occurs after an angioplasty procedure has been performed is the development of restenosis at, or near, the original site of the stenosis. When restenosis occurs, a second angioplasty procedure or even bypass surgery may be required, depending upon the degree of restenosis. In order to prevent the need to perform bypass surgery or subsequent angioplasty procedures, various devices and procedures have been developed for reducing the likelihood of development of restenosis after arterial intervention. For example, an expandable tube (commonly termed "stent") designed for permanent implantation within the body lumen has been utilized to help prevent restenosis. By way of example, several stent devices and methods can be found in commonly assigned and commonly owned U.S. Pat. No. 5,158,548 (Lau et al.); U.S. Pat. No. 5,242,399 (Lau et al.); U.S. Pat. No. 5,344,426 (Lau et al.); U.S. Pat. No. 5,421,955 (Lau et al.); U.S. Pat. No. 5,514,154 (Lau et al.); and U.S. Pat. No. 5,360,401 (Turnlund et al.), which are incorporated in their entirety herein.

More recent devices and procedures for preventing restenosis after arterial intervention employ the use of a radiation source to minimize or eliminate proliferation of cells which is thought to be a major factor in the restenotic process. Balloon catheters have been suggested as a means to deliver and maintain the radiation source in the area where arterial intervention has taken place, exposing the area to a sufficient radiation dose to abate cell proliferation. One such device and method are described in International Publication WO 95/19807 (Weinberger). Other devices and methods which utilize radiation treatment delivered by an intravascular catheter are disclosed in commonly-owned and assigned co-pending U.S. Ser. No. 08/654,698, filed May 29, 1996, entitled Radiation-Emitting Flow-Through Temporary Stent, which is incorporated herein by reference. Another medical device for the treatment of a body lumen by radiation is disclosed in European Pat. Ap. 0 688 580 A1 (Schneider).

Up to now, the radiation source has typically been in the form of a radioactive tipped source wire. Presently, such source wires are typically formed by permanently attaching a radiation source to the distal end of a wire. Typically, the radiation source is a solid structure having little or no longitudinal flexibility. This lack of flexibility may increase the difficulty of guiding the distal end of the source wire through small diameter and tortuous body lumens, requiring more effort and time to properly locate the radiation source adjacent an area of restenosis for treatment.

Additionally, presently available radioactive source wires cannot be sterilized for a variety of technical reasons, primarily issues associated with handling a long radioactive component. Thus, contact by the source wire with the patients blood stream had to be avoided to prevent contamination and possible resultant infection. Accordingly, radioactive source wires have been introduced into a patients coronary arteries using catheters such as the Schneider device, which includes a lumen that extends from a proximal opening to an area near the distal end of the catheter, where it "dead ends." This lumen, known as a "blind" or "dead end" lumen, is intended to carry the radioactive tipped source wire that slides into the lumen once the catheter is in place in the artery or body lumen. When the source wire is positioned, the radioactive section at the distal tip lies near the dead end to provide radiation to the body lumen. The inclusion of a "blind" lumen, however, increases the diameter of the catheter, adds complexity to the catheter, and increases the cost to manufacture the catheter.

What has been needed and heretofore unavailable in catheters which provide treatment of the body lumen with a radiation source is an intravascular catheter which utilizes sterile radiation source wires inserted through a lumen open to the blood stream. These source wires would include a removable tip incorporating a radiation source and a flexible, steerable distal end portion. The flexible, removable radiation source tip would be mounted on either a re-sterilizable or disposable core member. Such an intravascular catheter would avoid the requirement of a separate, closed lumen and thus could be manufactured with lower profiles than currently available catheters having "blind" lumens. Such an intravascular catheter would have to be easy and inexpensive to manufacture. Additionally, the core member and source wire dispenser should be re-sterilizable or disposable and the detachable tip including that radiation source should be able to be sterilized numerous times, so as to afford multiple use. The present invention fulfills these and other needs.

SUMMARY OF THE INVENTION

The invention provides a radiation source wire using a detachable tip and radiation source which allows the introduction of a sterilizable and re-usable radioactive tipped source wire to treat a vascular location of interest in a patient, such as where a vessel has become re-stenosed subsequent to a prior intravascular procedure.

In accordance with the present invention, the source wire includes a detachable tip including a radiation source that may be detached from a core member to be resterilized. The core member, including a source wire dispenser mounted on a remote afterloader, may be resterilized or disposable.

In another aspect of the invention, the detachable tip includes a flexible portion to improve the maneuverability of the radioactive source wire as it is guided through the body lumen. This flexible portion allows the radioactive source to be positioned to treat an area of restenosis in less time and with less difficulty than presently available source wires.

Other features and advantages of the invention will become apparent from the following detailed description, taken in conjunction with the accompanying drawings, which illustrate, by way of example, the features of the invention.

BRIEF DESCRIPTION OF THE DRAWINGS

In the drawings, where like reference numerals indicate like or similar components, elements and features across the several figures:

FIG. 1A is an enlarged partial cross-sectional view of the detachable radioactive tip of FIG. 1.

FIG. 2 is a cross-sectional view of the source wire of FIG. 1 depicting the radiation source located in the detachable tip of the source wire located adjacent a vasculature area to be treated.

FIG. 3 is an elevational view, partially in cross-section, of the detachable tip of the present invention illustrating an alternative method of mounting the core member to the source wire.

DETAILED DESCRIPTION OF THE PREFERRED EMBODIMENTS

Figure 1:
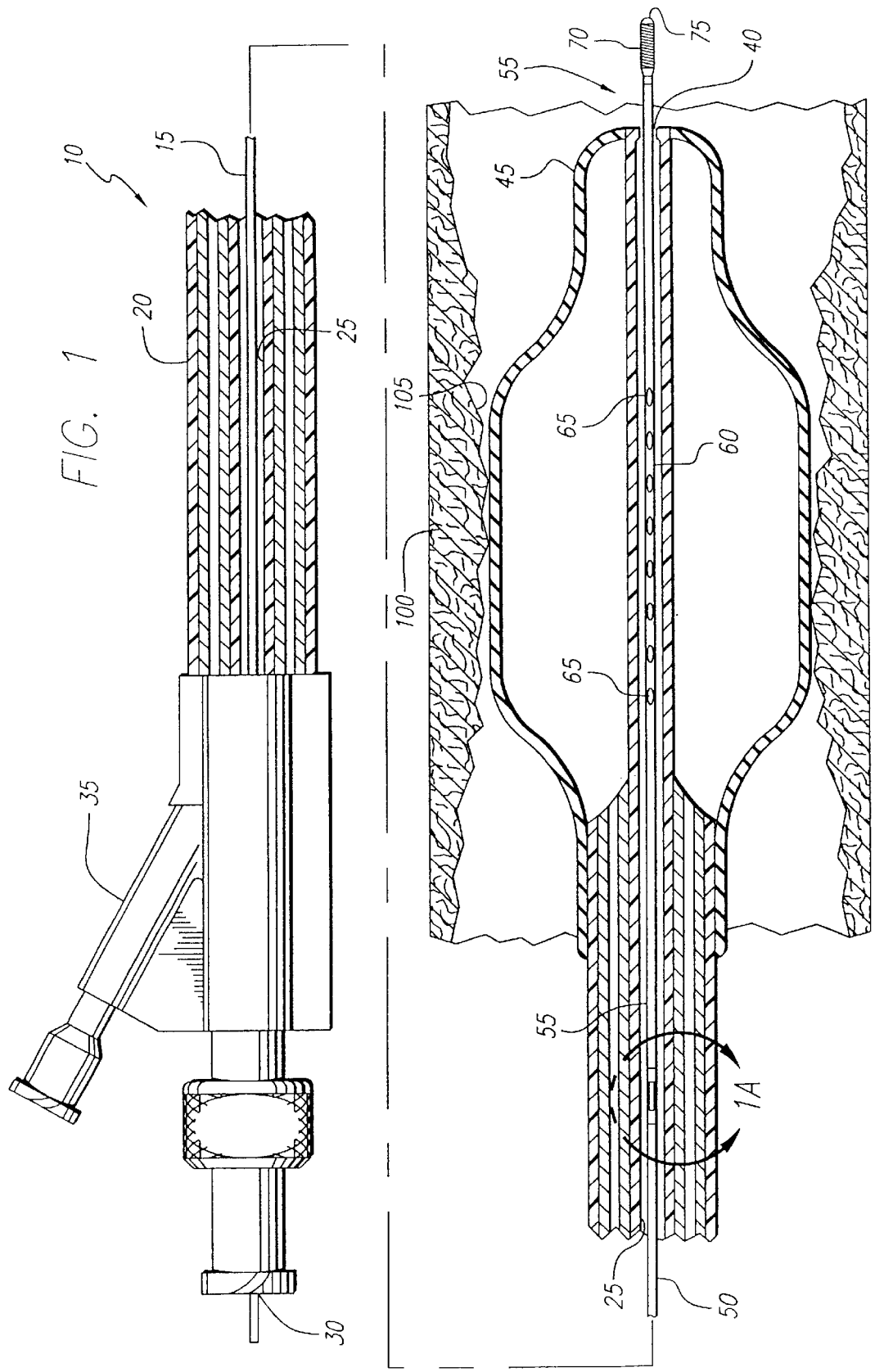
FIG. 1 is an elevational view, partially in cross-section, of a radiation source wire embodying features of the invention shown extending through a catheter.

As shown in the drawings for purposes of illustration, the invention is embodied in a radioactive intravascular source wire adapted to deliver a radiation source to a body lumen, such as a coronary artery. The source wire includes a detachable tip portion mounted at a distal end of the core member, a proximal end of the detachable tip being formed to receive a radioactive source and a distal end of the detachable tip including a flexible portion to improve the tracking of the radioactive source wire as it is advanced through a catheter towards an area of a body lumen to be treated. While the invention is described in detail as applied to the coronary arteries, those skilled in the art will appreciate that it can be used in other body lumens as well, such as peripheral arteries and veins. Where different embodiments have like elements, like reference numbers have been used.

FIGS. 1–3 illustrate an intravascular catheter assembly 10 including a radioactive source wire assembly 15 embodying features of the invention. The catheter assembly 10 generally includes an elongated catheter body 20 having a guide wire lumen 25 which extends from a guide wire port 30 located in a handpiece 35 mounted on a proximal end of the elongated catheter body 20 and a second guide wire port 40 located at a distal end 45 of the elongated catheter body 20. Both of these guide wire ports 30 and 40 are in fluid communication with the guide wire lumen 25. The radioactive source wire 15 is slidably disposed within the guide wire lumen 25.

The radioactive source wire 15 comprises a core member 50 and a detachable radioactive tip 55 mounted on a distal end of the core member 50. The detachable radioactive tip 55 includes a proximal portion 60 incorporating radioactive elements 65 and a flexible distal portion, preferably formed from a helical coil 70 or other flexible body. A rounded plug 75, preferably formed of radiopaque material, may be provided at the distal tip of coil 70 to assist in determining the location of radioactive tip 55 as it is advanced within the body lumen. The radioactive source wire 15 is intended to extend through the guide wire lumen 25 and partially out distal port 40.

The detachable radioactive tip 55 may be mounted to the distal end of the source wire 15 in a variety of manners. In one embodiment, illustrated in FIG. 1A, the proximal end of the detachable radioactive tip 55 has a tongue portion 80 that is sized to be recieved by a socket located at the distal end of the source wire 15. The tongue 80 and the socket 85 may be formed with complimentary threads 86,87 to allow the detachable tip 55 to be screwed onto the distal end of the source wire 15. As will be immediately apparent to those skilled in the art, other forms of attachment are also possible, limited only by the requirement that the attachment be capable of maintaining the detachable radioactive tip 55 on the distal end of the core member 15 as the core member 15 is advanced and retracted through the guide wire lumen 25 of the catheter body 20.

An alternative attachment configuration is illustrated by FIG. 2. In this embodiment, the distal end of the core member 15 is formed with a threaded tongue 90 that is sized to be removably inserted into socket 95 formed in the proximal end of the detachable radioactive tip 55.

Radioactive source wires are typically wound about a spool or other remotely controllable structure that is part of a device commonly known as a remote afterloader. The remote afterloader may be controlled by a physician or technician to advance or retract the radioactive core member 15 within the elongated body 20 of catheter 10. The flexible distal portion of the detachable radioactive tip 55 enhances the ability of the distal tip of the core member 15 in following the guide wire lumen 25 of the elongated body 20 of the catheter 10 through the tortuous pathway of a body lumen.

Referring again to FIG. 1, radioactive elements 65 may be embedded in or attached to the detachable radioactive tip 55. Alternatively, the proximal portion 60 of the detachable radioactive tip 55 may be formed from a radioactive material, or a non-radioactive member coated with a radioactive material. In a presently preferred embodiment, the radioactive source wire 15, including the detachable radioactive tip 55, may be sterilized so that contact with the patient's blood stream need not be avoided. Additionally, core member 15 and tip 55 may be formed from materials capable of withstanding repeated sterilization, enabling use of the core member 15 and tip 55 for multiple treatment procedures, thus reducing the cost of the procedure.

Referring now to FIGS. 1 and 3, in a preferred method of delivering a radioactive dose to a coronary artery, the distal end of the guide wire (not shown) is inserted through port 30 in the manipulation handle 35 (FIG. 1) leading into the guide wire lumen 25 and through the catheter's elongated body 20 until it emerges from port 40 located at the distal end of the catheter body 20. The guide wire is then advanced into the patient's arterial system until the guide wire is positioned across the portion of the arterial passageway 100 (FIG. 3) where a previous PCTA or atherectomy procedure was performed, designated target area 105 (FIG. 3), where a restenosis of the vessel is likely to develop. The proximal end of the guide wire is then manually held while catheter body 20 is advanced over the guide wire through a previously positioned guiding catheter to target area 105 within the patient's blood vessel.

Once the distal end of the catheter body 20 is in position, the guide wire is withdrawn and the distal end of the radioactive source wire 15 bearing the detachable radioactive tip 55 is inserted into port 30 of the manipulation handle 20 (FIG. 1) and into the guide wire lumen 25. The radioactive source wire 15 is advanced through the patient's vasculature, the flexible distal end 70 of the detachable tip 55 tracking through the guide wire lumen 25, until the radioactive proximal portion 60 of the detachable tip 55 is positioned at target area 105 of coronary artery 100 to receive the radiation dose.

The catheter 10 may also include an expandable region (not shown) located at the distal end of elongated catheter body 20. The expandable region of the catheter body 20 may be expanded when the detachable radioactive tip 55 is in position at target area 105 to hold the distal end of catheter 10 in place and to center radioactive tip 55 within artery 100. The expandable region is left expanded long enough to allow a sufficient radiation dose to destroy cells in target area 105 which cause the development of restenosis. While the present invention has been illustrated using an inflatable type catheter, it will be understood by those skilled in the art that where treatment times longer than a few minutes are required, the present invention may be combined with catheters having expandable regions that allow for continuous perfusion of blood past the treatment site to maintain the health of tissue dependent on the blood supplied by the vessel being treated.

After the radiation dose has been administered to target area 105, radiation core member 15 can be removed, the expanded region of catheter body 20 may be deflated and contracted, and catheter body 20 then withdrawn and removed from within the patient's vasculature.

The catheter assembly of the invention may be formed of conventional materials of construction which are described in detail in the prior art patents referenced herein. The material forming the catheter body and the expandable region can be made of any polymer with ductile properties which would be acceptable for the specific needs of the intravascular devices. Specifically, the material chosen for the catheter body and the expandable region would preferably provide sufficient hoop strength for the expandable region to center the catheter and radiation source wire while having enough flexibility to easily advance and navigate through tortuous anatomy. In addition, the portion of the material used to form the expandable region would preferably be sufficiently thin to allow the expandable region to expand easily. For example, catheter body 20 and the expandable region can be made of thin stainless steel tubing, nickel titanium alloy, polymer tubing and the like.

As described herein, the catheter assembly will deliver a low dosage of radiation to the body lumen, such as a coronary artery. It is preferred that a low activity source, on the order of 0.05 up to 3.0 curies be the typical activity source provided to treat, for example, target area 105 (FIG. 3) in a coronary artery. Preferably, 0.05 to 1.0 curies will provide the proper radiation dose level over a predetermined time.

The radiation delivered to a coronary artery should be in the range from about 10 to 3,000 rads in preferably not less than two minutes. The radiation dose can be delivered in less than two minutes, however, longer treatment times may result in tissue damage downstream of the treatment site due to obstruction of blood flow by the expandable member of catheter body 20.

It is contemplated that different radiation sources can be used, and the preferred radiation sources include for example iridium$^{192}$, cobalt$^{60}$, vanadium$^{48}$, gold$^{198}$, and phosphorus$^{32}$. It is also contemplated that whichever radiation source is used, that it have a half life of approximately less than one hundred days. Further, it is contemplated that the radiation sources emit either beta or gamma particles to kill the target cells, however, alpha-emitting radiation also can be used even though alpha radiation does not travel very far in human tissue.

From the foregoing, it will be appreciated that the radioactive source wire of the present invention provides for safe delivery of the a low dosage of radiation to a previously stenosed portion of a body lumen using a re-sterilizable and re-usable radiation source without requiring the inclusion of a "blind" lumen in a catheter. Since isolation of the radiation source from the patient's blood is no longer necessary, the radiation source may be inserted through the same lumen as is used to slide the catheter over the guide wire, the "blind" lumen maybe omitted, reducing the overall complexity and diameter of the catheter. Moreover, the detachable tip allows for using different methods to re-sterilize the remote afterloader and the core member body of the source wire and the detachable tip, thus ensuring that appropriate sterilization, without damage, can be accomplished prior to reuse. Further, the flexible tip of the detachable radioactive tip ensures that the detachable radioactive tip will easily and accurately track through the guide wire lumen of the catheter body when the source wire is advanced or retracted through the guide wire lumen.

Other modifications can be made to the present invention without departing from the scope thereof. The specific dimensions, dosages, times, and materials of construction are provided as examples and substitutes are readily contemplated which do not depart from the invention.

What is claimed is:

1. A radiation source delivery device for treatment of a body lumen, comprising:
   an elongated member;
   a removable tip having a radiation source and being removably attached to a distal end of the elongated member;
   a catheter having an open ended lumen extending therethrough, the open ended lumen having a distal opening and being configured to receive the elongated member and to allow the removable tip to extend at least partially through the distal opening, the removable tip being configured to remain attached to the distal end of the elongated member when extended through the distal opening.

2. The device of claim 1, wherein the radiation source is configured for delivering a low dosage of radiation to the body lumen at a selected position within the lumen.

3. The device of claim 2, wherein the level of the radiation delivered is in the range of about 10 to 3000 rads.

4. The radiation source delivery device of claim 1 wherein said catheter has an expandable region to substantially center said elongated member in said body lumen.

5. The device of claim 1, wherein the elongated member is configured to be sterilizable.

6. The device of claim 1, wherein the elongated member is configured to be re-usable.

7. The device of claim 1, wherein the removable tip is formed of a relatively stiff proximal section and a substantially flexible distal end.

8. The device of claim 1, wherein the removable tip is configured to be re-sterilizable.

9. The device of claim 7, wherein the removable tip is configured to be re-sterilizable.

10. The radiation source delivery device of claim 1 wherein said elongated member further comprises a flexible portion terminating in a radiopaque plug.

11. The radiation source delivery device of claim 10 wherein the radioactive source includes a radioactive source taken from the group of radioactive sources having a half-life of less than about one hundred days.

12. The device of claim 11, wherein the group of radiation sources includes iridium$^{192}$, cobalt$^{60}$, vanadium$^{48}$, gold$^{198}$, and phosphorus$^{32}$.

13. The radiation source delivery device of claim 11, wherein the group of radiation sources includes alpha-, beta-, and gamma-emitting radiation sources.

14. The radiation source delivery device of claim 10 wherein said radioactive source is located at a distal portion of said source wire.

15. The radiation source delivery device of claim 10 wherein said flexible portion comprises a helical coil.

16. The radiation source delivery device of claim 10 wherein said radioactive source is removably attached to the distal end of said source wire.

17. A method of radiotherapy comprising:
positioning a radiation delivery device in a body lumen, the radiation delivery device having:
an elongated member with a distal end;
a removable tip having a radiation source and being removably attached to the distal end of the elongated member; and
a catheter having a catheter lumen extending there through, the catheter lumen having a distal opening and being configured to slidably receive the elongated member and to allow the removable tip to extend through said distal opening;
advancing the removable tip through the catheter lumen to at least partially extend through the distal opening for delivering a radiation dose to a wall of the body lumen while the removable tip remains connected to the distal end of the elongated member; and
withdrawing the radiation delivery device from the body lumen after the radiation dose has been delivered.

18. The method of claim 17 wherein said distal end of said elongated member further comprises a flexible portion terminating in a radiopaque plug.

19. The method of claim 18, wherein said radioactive source delivers a low dose of radiation to said treatment area.

20. The method of claim 19, wherein the low dose of radiation is in a range of approximately 10 to approximately 3000 rads.

21. The method of claim 19, wherein the radiation source is exposed to the body lumen for no less than one minute.

22. The method of claim 19, wherein the radiation source is taken from the group of iridium$^{192}$, cobalt$^{60}$, vanadium$^{48}$, gold$^{198}$, and phosphorus$^{32}$.

23. A radiation source delivery device including a source wire, said source wire comprising:
a removable tip;
a flexible portion of said removable tip; and
a radioactive source of said removable tip, a portion of said source wire to extend through a distal opening of a catheter of said radiation source delivery device for radiation delivery, said removable tip to remain attached to the radiation source delivery device during said radiation delivery.

24. A method of radiotherapy comprising:
providing a source wire; and
advancing a distal portion of said source wire to a treatment area of a vessel and through a distal opening of a catheter to provide said radiotherapy, said distal portion of said source wire having a removable tip with a flexible portion and a radioactive source, said removable tip to remain attached to said source wire during said radiotherapy.

* * * * *